United States Patent [19]

Okahata

[11] Patent Number: 5,049,808
[45] Date of Patent: Sep. 17, 1991

[54] METHOD OF DETERMINING THE AMOUNT OF THE SUBSTANCES OR IONS CONTAINED IN AN IONIC SOLUTION OR A NON-DEIONIZED SOLUTION AND A ONE-SIDEBARRIER-COVERED CRYSTAL OSCILLATOR USED THEREFOR

[75] Inventor: Yoshio Okahata, Kanagawa, Japan

[73] Assignee: Sogo Pharmaceutical Company Limited, Tokyo, Japan

[21] Appl. No.: 404,513

[22] Filed: Sep. 8, 1989

[30] Foreign Application Priority Data

Sep. 10, 1988 [JP] Japan .................. 63-225551
Aug. 31, 1989 [JP] Japan .................. 1-223191
Aug. 31, 1989 [JP] Japan .................. 1-223192

[51] Int. Cl.$^5$ .................. G01N 27/414; H01L 41/00
[52] U.S. Cl. .................. 324/71.1; 324/439; 73/24.06; 310/311
[58] Field of Search .................. 324/71.1, 71.4, 442, 324/438; 310/311, 312, 321, 322, 328; 436/178; 73/24.01, 24.06; 422/55

[56] References Cited

U.S. PATENT DOCUMENTS 3,266,291 8/1966 King, Jr. .................. 73/24.06
4,789,804 12/1988 Karube .................. 310/311

FOREIGN PATENT DOCUMENTS 0215669 3/1987 European Pat. Off. .
60-18743 1/1985 Japan .
8702066 4/1987 World Int. Prop. O. .

OTHER PUBLICATIONS

Muramatsu, Hiroshi et al., "Piezoelectric Crystal Biosensor ... Immunoglobulins", *Analytical Chemistry*, vol. 59, No. 23, Dec. 1, 1987, pp. 2760–2763.
Muramatsu, H. et al., "Determination of Microbes and Immunoglobulins Using a Piezoelectric Biosensor", *Journal of Membrane Science*, 41, 12 (1989), pp. 281–290.
"Behavior of Piezoelectric Quartz Crystal in an Aqueous Solution ... of Minute Amount of Cyanide", *The Chemical Society of Japan*, No. 10, 1980, pp. 1621–1625 (Summary in English on p. 1625).

Primary Examiner—Jack B. Harvey
Attorney, Agent, or Firm—Cushman, Darby & Cushman

[57] ABSTRACT

A method of determining the amount of the substances or ions contained in an ionic solution or a non-deionized solution by measuring the frequency of a one side barrier-covered crystal oscillator comprising a crystal oscillator, a barrier to cover over one of the electrodes of the crystal oscillator through a predetermined insulative space so as to prevent the ionic solution or the non-deionized solution from permeating therethrough and an adsorption film cast on the other electrode of the crystal oscillator, in situ in the state that the one side barrier-covered crystal oscillator is dipped in the ionic solution or the non-deionized solution, and the one side barrier-covered crystal oscillator used therefor.

4 Claims, 2 Drawing Sheets

METHOD OF DETERMINING THE AMOUNT OF THE SUBSTANCES OR IONS CONTAINED IN AN IONIC SOLUTION OR A NON-DEIONIZED SOLUTION AND A ONE-SIDEBARRIER-COVERED CRYSTAL OSCILLATOR USED THEREFOR

TITLE OF THE INVENTION

A Method of Determining the Amount of the Substances or Ions Contained in an Ionic Solution or a Non-Deionized Solution and a One Side Barrier-Covered Crystal Oscillator Used Therefor.

BACKGROUND OF THE INVENTION (1) Field of the Invention

This invention relates to a method of determining the amount of the substances or ions contained in an ionic solution or a non-deionized solution and a one side barrier-covered crystal oscillator used therefor, and more particularly to a method of determining in situ the amount of the substances or ions contained in an ionic solution or a non-deionized solution by use of a one side barrier-covered crystal oscillator.

(2) Description of the Prior Art

Determination of the amount of the substances or ions contained in an ionic solution or a non-deionized solution by use of the crystal oscillator has to be carried out by a process in which measurements of frequency of the crystal oscillator are effected in distilled water or deionized water separately from the ionic solution or the non-deionized solution, because the use of the crystal oscillator by dipping it into the ionic solution or the non-deionized solution as it is, causes substantially no oscillation, resulting in making substantially impossible the afore-mentioned determination, or making impossible accurate determination of the amount of the substances or ions contained in the ionic solution or the non-deionized solution, depending on the concentration of ions in the ionic solution or the non-deionized solution.

There have been proposed, for example, (1) a method of determining the amount of substances contained in the ionic solution or the non-deionized solution, which comprises setting a crystal oscillator in a flow cell, allowing distilled water to flow therethrough, allowing the ionic solution or the non-deionized solution to flow therethrough for adsorbing the substances contained therein onto the crystal oscillator, and allowing distilled water to flow therethrough for measuring the frequency of the crystal oscillator as used in the studies of the antigen-antibody reaction; (2) a method of determining the amount of ions contained in the ionic solution or the non-deionized solution, which comprises holding a crystal oscillator between two cells, filling one of the cells with the ionic solution or the non-deionized solution and the other with distilled water so that the ionic solution or the non-deionized solution and the distilled water may be brought into contact with each of the both electrodes of the crystal oscillator respectively, and measuring the frequency of the crystal oscillator as employed in the determination of the amount of the heavy metal ion; and (3) a method of determining the amount of ions contained in the ionic solution, which comprises setting horizontally the crystal oscillator, mounting a case on the upper side only of the crystal oscillator, filling the case with the ionic solution or the non-deionized solution, and measuring the frequency of the crystal oscillator as employed in the determination of the heavy metal ion.

Of these prior art methods, the first method (1) needs a large amount of ionic solution or non-deionized solution in the flow system and is disadvantageous when the adsorption and desorption take place reversibly, the second method (2) is based on the fact that the crystal oscillator is insensitive to the weight on a crystal plate part other than the electrode part, in other words, the fact that the crystal plate part other than the electrode part does not participate in oscillation, but raises problems of strength as the size of the cell is increased, because the crystal oscillator is formed by use of a thin crystal plate, and the third method (3) is based on the fact that the crystal oscillator is insensitive to the weight on the crystal plate part other than the electrode part as in the second method (2), but has such drawbacks as to make temperature control difficult and make stirring impossible.

SUMMARY OF THE INVENTION

It is an object of the present invention to provide a method of determining the amount of the substances or ions contained in the ionic solution or the non-deionized solution by use of a one side barrier-covered crystal oscillator, and the one side barrier-covered crystal oscillator used therefor, which are capable of determining the amount of the substances or ions contained in the ionic solution or the non-deionized solution by measuring the frequency of the one side barrier-covered crystal oscillator in situ in the state that the one side barrier-covered crystal oscillator is dipped in the ionic solution or the non-deionized solution with easy temperature control and stirring in the measurement of the frequency without needing a large amount of ionic solution or non-deionized solution and of distilled water or without using the large-sized cell, and to provide the one side barrier-covered crystal oscillator used therefor.

It is another object of the present invention to provide a method of determining the amount of odor substances and/or bitter substances contained in the ionic solution or the non-deionized solution by use of the one side barrier-covered crystal oscillator and by measuring its frequency in situ in the state that the one side barrier-covered crystal oscillator is dipped in the ionic solution or the non-deionized solution, and to provide the one side barrier-covered crystal oscillator used therefor.

It is still another object of the present invention to provide a method of determining the amount of the odor substances and/or bitter substances contained in the physiological saline solution as the ionic solution by use of a one side barrier-covered crystal oscillator and by measuring its frequency in situ in the state that the one side barrier-covered crystal oscillator is dipped in the physiological saline solution, and to provide the one side barrier-covered crystal oscillator used therefor.

It is still another object of the present invention to provide a method of determining the amount of the bivalent metal ions such as $Ca^{2+}$, $Mg^{2+}$, $Mn^{2+}$ and the like, particularly $Ca^{2+}$ ion contained in the serum or body fluids as the ionic solution by use of the one side barrier-covered crystal oscillator and by measuring its frequency in situ in the state that the one side barrier-covered crystal oscillator is dipped in the serum or body fluids, and to provide the one side barrier-covered crystal oscillator used therefor.

Firstly, the present invention provides a method of determining the amount of the substances or ions contained in an ionic solution or a non-deionized solution by use of a crystal oscillator, which method comprises covering over one of the electrodes of the crystal oscillator through a predetermined insulative space substantially without being brought into contact therewith with a barrier to prevent the ionic solution or the non-deionized solution from permeating therethrough, casting an adsorption film onto the other electrode of the crystal oscillator, dipping the one side barrier-covered crystal oscillator into the ionic solution or the non-deionized solution, adsorbing the substances contained in the ionic solution or the non-deionized solution onto the adsorption film or chemically bonding the ions therein with the adsorption film, and measuring frequency changes between before and after the adsorption or chemical bonding in situ in the state that the one side barrier-covered crystal oscillator is dipped in the ionic solution or the non-deionized solution to determine the amount of the substances or ions contained in the ionic solution or the non-deionized solution.

Secondly, the present invention provides a one side barrier-covered crystal oscillator used in the aforementioned method of determining the amount of the substances or ions contained in the ionic solution or the non-deionized solution, said one side barrier-covered crystal oscillator comprising a crystal oscillator, a barrier to cover over one of the electrodes of the crystal oscillator through a predetermined insulative space so as to prevent the ionic solution or the non-deionized solution from permeating therethrough, and an adsorption film cast on the other electrode of the crystal oscillator.

DETAILED DESCRIPTION OF THE INVENTION

Figure 1:
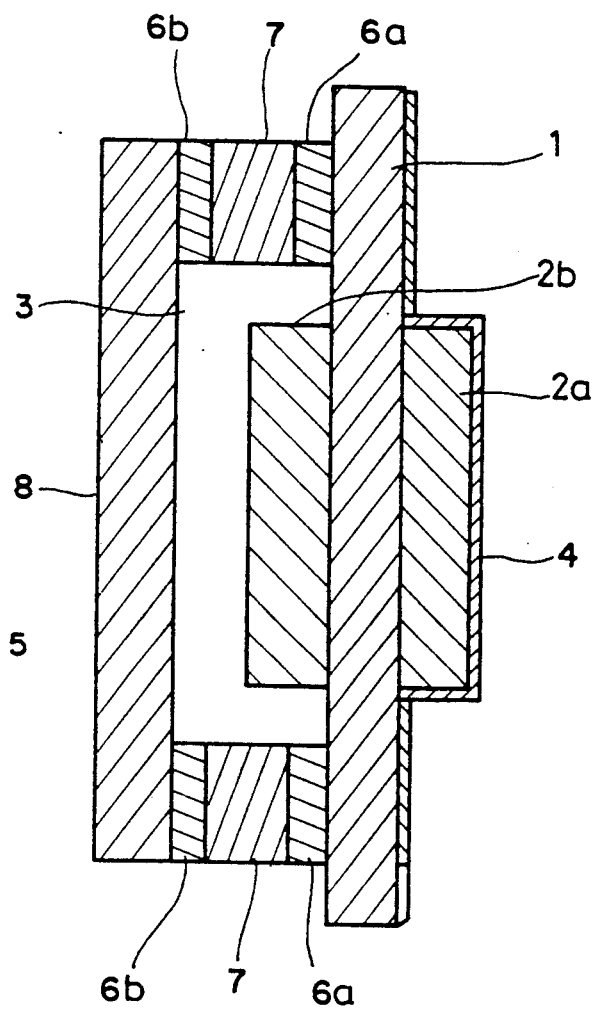
FIG. 1 is a cross-sectional view showing a first embodiment of the one side barrier-covered crystal oscillator of the present invention, where 1 is a crystal plate, 2a and 2b are electrodes, 6a and 6b are adhesives, 7 is a silicone rubber material, 3 is an insulative space, 8 is a plastic sheet, and 4 is an adsorption film a barrier 5 being composed of adhesive 6a and 6b, silicone rubber material 7 and plastic sheet 8.

The ionic solution in the present invention may be any solution which contains ion, normally at a concentration of 0.01M to 0.8M, and may include the ionic solutions which are generally used in the fields of electrochemistry and biochemistry. Examples of the ionic solution include ionic solutions used in studies of the antigen-antibody reaction, ionic solutions used in the determination of the amount of heavy metals, ionic solutions used in the determination of the amount of odor substances, bitter substances and the like, physiological saline solutions containing odor substances, bitter substances and the like, the serum or body fluids containing bivalent metal ions such as $Ca^{2+}$, $Mg^{2+}$, $Mn^{2+}$, etc., and the like.

The non-deionized solution used in the present invention may include any aqueous system, in which it is substantially impossible to measure the frequency of the crystal oscillator for the determination of the substances and/or ions contained therein as the crystal oscillator is dipped therein, such as aqueous solution, aqueous dispersion, aqueous emulsion, aqueous suspension and the like, except for distilled water and deionized water.

Examples of the non-deionized solution may include non-deionized water, non-deionized aqueous solution, non-deionized aqueous emulsion, non-deionized aqueous colloidal dispersion and the like.

Specific examples of the non-deionized solution may include alcoholic drinks such as beer, sake, whisky, low-class distilled spirits, wine and the like, drinks such as milk, milk with coffee, coffee, black tea, green tea and the like, soft drinks such as fruit juice, soda drinks and the like, tap water, sewage, river water, lacustrine water, and the like.

The substances contained in the ionic solution or the non-deionized solution and determined according to the method of the present invention include any substances which are adsorbed onto the adsorption film cast on the electrode of the crystal oscillator, and the amount of which is determined by measuring the frequency change due to the adsorption. Examples thereof include odor substances, bitter substances and the like.

The bitter substances used in the present invention are not specifically limited so long as they are adsorbed onto the adsorption film of the present invention, and may include acidic substances such as inorganic and organic acids, basic substances such as inorganic and organic bases, for example, caustic soda, ammonia, pyridine, triethylamine and the like, inorganic and organic salts, medicines, agricultural chemicals, and the like.

The typical examples of the bitter substances include strychnine, quinine, nicotine, phenylthiourea, papaverine, caffeine, naringin, octaacetyl sucrose, oligopeptide, and the like.

The odor substances used in the present invention are not specifically limited so long as they are adsorbed onto the adsorption film of the present invention, and, in a broad sense, may include perfumes, anesthetics, malodorants, medicines, agricultural chemicals, and the like.

The typical examples of the odor substances in a narrow sense include $\beta$-ionone, aliphatic alcohols such as octanol, camphor, amylacetate, vanilline, ethylbutylate, phenol, aldehydes, and the like.

Typical examples of the perfumes include P-anisaldehyde, 1-undecanol, anisalcohol, anisol, phenylethyl acetate, citral, methyl salicylate, benzyl acetate, tetrahydrogeraniol, terpineol, geranyl acetate, and the like.

Examples of the general anesthetics as the compounds having narcosism in the aforementioned anesthetics are shown in Table 1. In Table 1, potency is a value representing intensity of the anesthetics and is shown as values obtained by use of a tadpole.

TABLE 1

| No. | Anesthetic Compounds | Potency |
|---|---|---|
| 1 | methanol | 1.00 |
| 2 | ethanol | 2.43 |
| 3 | acetone | 3.47 |
| 4 | 1-propanol | 9.43 |
| 5 | butanone | $1.20 \times 10$ |
| 6 | diethyl ether | $2.99 \times 10$ |
| 7 | 1-butanol | $4.43 \times 10$ |
| 8 | paraldehyde | $5.44 \times 10$ |
| 9 | benzylalcohol | $5.01 \times 10^2$ |
| 10 | chloroform | $7.62 \times 10^2$ |
| 11 | 1-hexanol | $1.12 \times 10^3$ |
| 12 | halothane | $4.47 \times 10^3$ |
| 13 | methoxyflurane | $4.86 \times 10^3$ |
| 14 | 1-octanol | $7.93 \times 10^3$ |
| 15 | pentane | $1.51 \times 10^4$ |
| 16 | 1-nonanol | $4.03 \times 10^4$ |
| 17 | hexane | $6.75 \times 10^4$ |
| 18 | 1-decanol | $1.00 \times 10^5$ |

Examples of the malodorants include malodor-emitting substances selected from ketones, amines, imines, aldehydes such as acetaldehyde, organic acids and the like, sulfur compounds such as methyl mercaptan, hydrogen sulfide, methane sulfide, methyl disulfide and the like, styrene, mixtures thereof, malodor-emitting substances selected from various kinds of industrial wastes and mixtures thereof, foul breath-producing substances and mixtures thereof, and the like.

The ions contained in the ionic solution or the non-deionized solution and determined according to the method of the present invention include any ions which are chemically bonded with the adsorption film. Examples of the aforementioned ions include bivalent metal ions such as $Ca^{2+}$, $Mg^{2+}$, $Mn^{2+}$ and the like. For example, an immobilized bilayer film as the adsorption film selectively forms a complex with a phosphoethanolamine based phospholipid bilayer adsorption film to be specifically bonded therewith.

According to the method and the one side barrier-covered crystal oscillator of the present invention, one of the electrodes of the crystal oscillator is covered through a predetermined insulative space substantially without being brought into contact therewith with a barrier to prevent the ionic solution or the non-deionized solution from permeating therethrough, and an adsorption film is cast onto the other electrode of the crystal oscillator.

The electrode of the crystal oscillator used in the present invention may include a silver or aluminum electrode, which has a tendency to exhibit an unstable oscillation due to dissolution in the ionic solution or the like. Preferred examples of the electrode include those made of the inactive and depositable metals such as gold, platinum and the like.

The adsorption film, which is cast on the electrode and on which the substances contained in the ionic solution or the non-deionized solution are adsorbed to be used in the present invention, may include the immobilized bilayer film and a polymer film comprising a polymer alone, a mixture of polymers, or a mixture of the polymer or polymers with a monomer or a low molecular weight compound.

The immobilized bilayer film used as the adsorption film may include those prepared by immobilizing, by use of polymers, (i) synthetic lipids such as ammonium salts, sulfonates, carboxylates in the form of trialkyl, dialkyl and/or monoalkyl as represented by the formula:

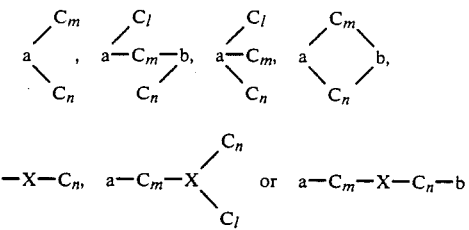

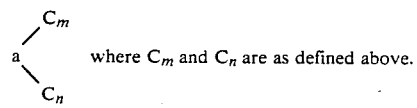

where a and b represent a hydrophilic group moiety such as $-N^+(CH_3)_3$, $-SO_3^-$, $PO_4^{31}$, polyol, polyether or the like, $C_l$, $C_m$ and $C_n$ represent a hydrophobic group moiety such as alkyl group, fluoroalkyl group, alkylene group having a $C_8$ or higher carbon chain in total, or the like, and X represents a rigid segment such as diphenylazomethine group, biphenyl group, naphthalene group, anthracene group or the like, and/or (ii) natural lipids such as phosphatidyl choline, phosphatidyl serine and the like as represented by the formula:

$$a\begin{matrix}\diagup C_m \\ \diagdown C_n\end{matrix}$$ where $C_m$ and $C_n$ are as defined above.

Specific examples of the immobilized bilayer film used in the present invention include (i) films prepared by blending the synthetic lipid and/or natural lipid with high-molecular compounds such as polyvinyl chloride, polystyrene, polycarbonate, polyvinyl alcohol, acetyl cellulose and the like, followed by casting; (ii) films prepared by impregnating pores of filters having a microporous structure such as miliporefilter, and the like, with a chloroform solution of the synthetic lipid and/or natural lipid, followed by drying; (iii) films obtained by dissolving a polyion complex powder prepared by mixing an aqueous dispersion of the synthetic lipid and/or natural lipid having a cationic, hydrophilic group with an aqueous solution of an anionic high-polymer such as polystyrene sulfonic acid, heparin, polyvinylsulfonic acid, polyacrylic acid, polyglutamic acid, and the like in chloroform, followed by casting; (iv) polyion complex type bilayer films composed of the lipid having an anionic hydrophilic group and cationic high polymer such as polyallylamine, polyethylene imine, quaternary polyaminostyrene and the like; (v) Langmuir-Blodgett type multibilayer films composed of the synthetic lipid and/or combined with high molecular compounds; (vi) combined films of (i)-(v) with a polymer film; (vii) combined films of (i)-(vi); and the like. The above film (vi) may prevent adverse effects due to moisture.

Examples of the immobilized bilayer film, which is cast on the electrode of the crystal oscillator and is chemically bonded with ions contained in the ionic solution, particularly the bivalent metal ions, include phosphoethanolamine based phospholipid bilayer film, and the like.

The polymers of the polymer films used as the adsorption film in the present invention may include synthetic organic polymers, natural organic polymers, synthetic inorganic polymers, and natural inorganic polymers. Examples of the above synthetic organic polymers include polystyrene, polyvinyl chloride, synthetic resins, synthetic rubber and the like. Examples of the above natural organic polymers include cellulose, starch, natural rubber, protein and the like. Examples of the above synthetic inorganic polymers include polychlorinated phosphonitrile and the like. Examples of the above natural inorganic polymers include mica, asbestos and the like.

Generally, the above polymer film selectively act depending on the types of the substances contained in the ionic solution or the non-deionized solution. For example, γ-methyl-L-glutamate is preferably used as the polymer film for lower aliphatic acid esters as the odor substances, polystyrene or polyvinyl chloride is preferably used as the polymer film for low molecular weight ketones as the odor substances, polyvinyl alcohol is preferably used as the polymer film for low molecular weight carboxylic acids as the odor substances, polystyrene is preferably used as the polymer film for styrene as a malodorant.

The polymer film used as the adsorption film, which is cast on the one side barrier-covered crystal oscillator and chemically bonds with ions contained in the ionic solution or the non-deionized solution, may include, for example, any polymer films having a functional group to bond with the ion.

The step of covering one of the electrodes of the crystal oscillator in the method of the present invention is not specifically limited so long as the electrode is covered through a predetermined insulative space substantially without being brought into contact therewith with a barrier to prevent the ionic solution or the non-deionized solution from permeating therethrough.

For example, according to a first embodiment of the step of covering the electrode as shown in FIG. 1, electrodes 2a and 2b are deposited on a crystal plate 1, and the electrode 2b is covered thereover with a barrier 5 which is formed by adhering a silicone rubber or plastic material 7 on the crystal plate 1 around the electrode 2b with a silicone based polymer adhesive 6a followed by adhering thereon a plastic sheet 8 with a silicone based polymer adhesive 6b, or by adhering the plastic sheet 8 on the silicone rubber or plastic material 7 with the silicone based polymer adhesive 6b followed by adhering the silicone rubber or plastic material 7 on the crystal plate 1 around the electrode 2b with the silicone based adhesive 6a so that the electrode 2b may be covered through a predetermined insulative space 3 with the barrier thus formed substantially without being brought into contact therewith. An adsorption film 4 is cast on the electrode 2a.

Figure 2:
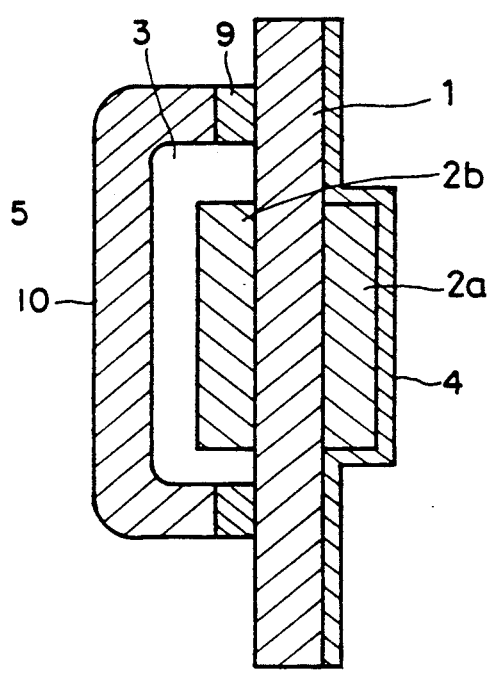
FIG. 2 is a cross-sectional view showing a second embodiment of the one side barrier-covered crystal oscillator of the present invention, where 1 is a crystal plate, 2a and 2b are electrodes, 9 is an adhesive, 3 is an insulative space, 10 is a plastic sheet cover, and 4 is an adsorption film a barrier 5 being composed of adhesive 9 and plastic cover sheet 10.

According to a second embodiment of the step of covering the electrode as shown in FIG. 2, the electrode 2b is covered with a barrier 5 which is formed by adhering a plastic sheet cover 10 onto the crystal plate 1 around the electrode 2b with a silicone based polymer adhesive 9 so as to be sealed and form a predetermined insulative space 3.

Figure 3:
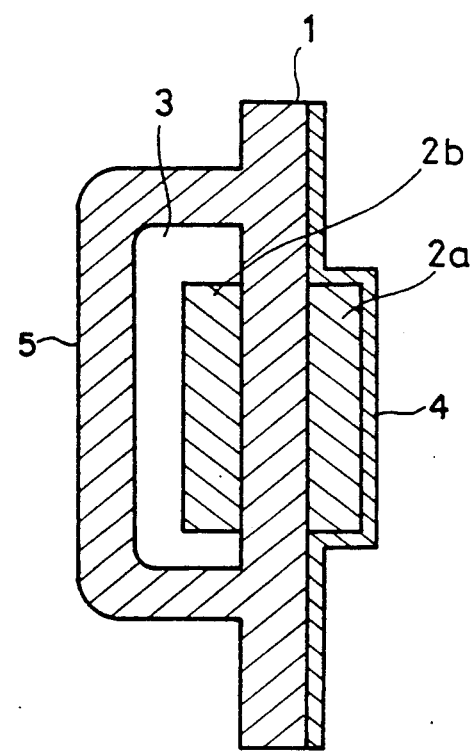
FIG. 3 is a cross-sectional view showing a third embodiment of the one side barrier-covered crystal oscillator of the present invention, where 1 is a crystal plate, 2a and 2b are electrodes, 3 is an insulative space, 5 is a barrier formed integrally with the crystal plate 1, and 4 is an adsorption film.

According to a third embodiment of the step of covering the electrode as shown in FIG. 3, the electrode 2b is covered with a barrier 5 formed integrally with the crystal plate 1 so as to cover the electrode 2b through a predetermined insulative space 3.

The predetermined insulative space is not specifically limited, so long as electrical conductivity between both electrodes is broken therethrough, but normally in the range of 0.5 to 5 mm, preferably 1 to 2 mm as a distance from the surface of the electrode in the vertical direction to the surface of the electrode.

When the above insulative space is less than 0.5 mm, breaking of electrical conductivity between both electrodes may be unsatisfactory. When the above insulative space is more than 5 mm, it is not only be technically meaningless, but also may cause troubles in use.

The present invention makes it possible to provide a method of determining the amount of the substances such as odor substances and bitter substances as well as ions such as $Ca^{2+}$, $Mg^{2+}$, $Mn^{2+}$ and the like contained in the ionic solution or the non-deionized solution by use of a one side barrier-covered crystal oscillator, which method is capable of determining the amount of the substances and ions contained in the ionic solution or the non-deionized solution with the same precision in the order of nanogram as in the distilled water or deionized water by measuring the frequency of the one side barrier-covered crystal oscillator in situ in the state that the one side barrier-covered crystal oscillator is dipped in the ionic solution or the non-deionized solution with easy temperature control and stirring in the measurement of the frequency without needing a large amount of ionic solution or non-deionized solution and of distilled water or without using the large-sized cell as in the prior art, and to provide the one side barrier-covered crystal oscillator used therefor.

An example of the determination of the amount of bitter substances contained in the ionic solution according to the present invention shows that the enzymatic decomposition of food such as protein often produces oligopeptides having a bitter taste to raise problems from the standpoint of taste in the presence of a large amount of ions during the enzymatic decomposition of food, whereas the use of the one side barrier-covered crystal oscillator of the present invention makes it possible to determine the amount of the bitter substances while carrying out the enzymatic decomposition reaction with the result that the one side barrier-covered crystal oscillator of the present invention is capable of being used as a sensor for reducing the production of bitter substances under controlled conditions.

The present invention makes it possible to provide a method of determining the amount of the odor substances and/or bitter substances contained in the physiological saline solution or the blood as the ionic solution with the same precision in the order of nanogram as in the distilled water or deionized water by use of the one side barrier-covered crystal oscillator and by measuring its frequency in situ in the state that the one side barrier-covered crystal oscillator is dipped in the physiological saline solution or the blood, and to provide the one side barrier-covered crystal oscillator used therefor. That is, the determination of the amount of anesthetics contained in the blood, for example, means that the determination of the amount of anesthetics actually contained in the blood of a patient under operation by an inhalational anesthesia is made possible directly in situ with precision.

The present invention makes it possible to provide a method of determining the amount of the bivalent metal ions such as $Ca^{2+}$, $Mg^{2+}$, $Mn^{2+}$ and the like, particularly $Ca^{2+}$ ion contained in the serum or body fluids as the ionic solution with the same precision in the order of nanogram as in the distilled water or deionized water by use of the one side barrier-covered crystal oscillator and by measuring its frequency in situ in the state that the one side barrier-covered crystal oscillator is dipped in the serum or body fluids, and to provide the one side barrier-covered crystal oscillator used therefor.

From the fact that the amount of $Ca^{2+}$ ion contained in the blood and body fluids is increased when man gets ill and a precise determination of the amount of $Ca^{2+}$ ion therein is important from the standpoint of health control, the aforementioned effect of the present invention is very useful from the standpoint of human health control.

The present invention will be explained more in detail by the following Examples and Comparative Examples.

EXAMPLE 1

Dialkyl ammonium salt ion ($2C_{18}N^+2C_1$) from dioctadecyldimethylammonium bromide $2C_{18}N^+2C_1Br^-$ and polystyrene sulfonic acid ion ($PSS^-$) from sodium poly(styrene-sulfonate) $PSS^-Na^+$ are reacted at 70° C. to form precipitates of a polyion complex, followed by reprecipitation and drying. In FIG. 1, the polyion complex thus obtained is dissolved in chloroform and cast to a thickness of 0.5 μm as an immobilized bilayer film on one electrode 2a of 5 mmπ electrodes 2a and 2b on both sides of a crystal plate 1 of a gold-electrode—9.00 MHz, AT-cut crystal oscillator. A silicone based polymer adhesive is coated around spaced in the radial direction by about 3 mm from the periphery of the electrode 2b on another side of the crystal plate 1, a silicone rubber plate 7 of 10 mm in length, 10 mm in width and 3 mm in thickness, a central part of which is hollowed out in the form of a circle of about 6 mm in diameter, is placed thereon to be sealed, the same adhesive 6b as the aforementioned adhesive 6a is then coated thereon, a plastic plate 8 having a thickness of 0.2 to 1 mm is placed on the adhesive 6b to be sealed and to form an insulative space 3 and a barrier comprising the adhesives 3a, the silicone rubber plate 7, the adhesive 6b and the plastic plate 8, resulting in obtaining a one side barrier-covered crystal oscillator, one of the electrodes of which is covered with the barrier formed as above through the insulative space 3.

EXAMPLE 2

To a physiological saline solution is added 20 ppm of halothane as the anesthetics to be subjected to the following experiment.

The one side barrier-covered crystal oscillator obtained in Example 1 is dipped into distilled water to measure its frequency. Thereafter, it is dipped into the physiological saline solution to adsorb the halothane onto the immobilized bilayer film and to measure its frequency as it is with the result that frequency change due to adsorption of halothane is 115 Hz corresponding to 121 ng of halothane adsorbed.

COMPARATIVE EXAMPLE 1

The same frequency measurement procedures as in Example 2 are repeated except that the crystal oscillator is not covered with the barrier, resulting in producing no oscillation and in making the frequency measurement impossible.

COMPARATIVE EXAMPLE 2

The procedures of Example 2 are repeated except that the crystal oscillator is not covered with the barrier and that frequency measurements only are carried out in distilled water with the result that a frequency change due to adsorption of halothane is 120 Hz corresponding to 126 ng of halothane adsorbed.

It is clear from the above results that Example 2 provides substantially the same results as in Comparative Example 2.

EXAMPLE 3

The same experiment as in Example 2 is repeated except for using 20 ppm of strychnine as bitter substances with the result that frequency change due to adsorption is 390 Hz corresponding to 410 ng of strychnine adsorbed.

COMPARATIVE EXAMPLE 3

The same frequency measurement procedures as in Example 3 are repeated except that the crystal oscillator is not covered with the barrier, resulting in producing no oscillation and in making the frequency measurement impossible.

COMPARATIVE EXAMPLE 4

The same procedures as in Example 3 are repeated except that the crystal oscillator is not covered with the barrier and that the frequency measurement only is carried out in distilled water, resulting in that frequency change due to adsorption is 400 Hz corresponding to 420 ng of strychnine adsorbed.

EXAMPLE 4

The procedures of Example 2 are repeated except that the frequency of the barrier-covered crystal oscillator obtained in Example 1 is measured in situ in the state that the barrier-covered crystal oscillator is dipped in an aqueous buffer solution having an ion concentration of 0.1M and pH 7-8, and containing 20 ppm of oligopeptide, a bitter substance, formed by enzymatically decomposing polysaccharide such as cellulose in the presence of an enzyme such as cellulase to determine the amount of the oligopeptide to be adsorbed, resulting in that frequency change due to adsorption is 40 Hz corresponding to 42 ng of oligopeptide adsorbed.

COMPARATIVE EXAMPLE 5

The same frequency measurement procedures as in Example 4 are repeated except that the crystal oscillator is not covered with the barrier, resulting in producing no oscillation and in making the frequency measurement impossible.

COMPARATIVE EXAMPLE 6

The same procedures as in Example 4 are repeated except that the crystal oscillator is not covered with the barrier and that the frequency measurement only is carried out in distilled water, resulting in that frequency change due to adsorption is 40 Hz corresponding to 42 ng of oligopeptide adsorbed.

EXAMPLE 5

The frequency of a one side barrier-covered crystal oscillator obtained in the same manner as in Example 1 except that a 1,3-ditetradecyl-glycerophosphoethanolamine bilayer film is used, is measured in situ in the state that the one side barrier-covered crystal oscillator is dipped in the blood to determine an amount to be chemically bonded of $Ca^{2-}$ ion contained in the blood at a concentration of 100 ppm in the same manner as in Example 2, resulting in that frequency change due to chemical bonding is 47 Hz corresponding to 49 ng of $Ca^{2-}$ ion chemically bonded with the immobilized bilayer film.

COMPARATIVE EXAMPLE 7

The same frequency measurement procedures as in Example 5 are repeated except that the crystal oscillator is not covered with the barrier, resulting in producing no oscilation and in making the frequency measurement impossible.

COMPARATIVE EXAMPLE 8

The same procedures as in Example 5 are repeated except that the crystal oscillator is not covered with the barrier and that the frequency measurement only is carried out in distilled water, resulting in that frequency change due to chemical bonding is 50 Hz corresponding to 53 ng of $Ca^{2+}$ ion chemically bonded with the immobilized bilayer film.

It is clear from the above results that Example 5 provides substantially the same results as in Comparative Example 8.

EXAMPLE 6

The one side barrier-covered crystal oscillator obtained in Example 1 is dipped into distilled water to measure its frequency. Thereafter, it is dipped into a commercially available beer to adsorb odor substances and bitter substances contained therein onto the immobilized bilayer film and to measure its frequency as it is, resulting in that frequency change due adsorption 1600 Hz corresponding to 1680 ng of odor substances and bitter substances adsorbed.

COMPARATIVE EXAMPLE 9

The same frequency measurement procedures as in Example 6 are repeated except that the crystal oscillator is not covered with the barrier, resulting in producing no oscillation and in making the frequency measurement impossible.

EXAMPLE 7

Procedures of Example 6 are repeated except that a marketed sake in place of the beer is used with the result that frequency change due to adsorption is 1300 Hz corresponding to 1365 ng of odor substances and bitter substances adsorbed.

COMPARATIVE EXAMPLE 10

The same frequency measurement procedures as in Example 7 are repeated except that the crystal oscillator is not covered with the barrier, resulting in producing no oscillation and in making the frequency measurement impossible.

EXAMPLE 8

Procedures of Example 6 are repeated except that a marketed milk in place of the beer is used with the result that frequency change due to adsorption is 2700 Hz corresponding to 2835 ng of odor substances and bitter substances adsorbed.

COMPARATIVE EXAMPLE 11

The same frequency measurement procedures as in Example 8 are repeated except that the crystal oscillator is not covered with the barrier, resulting in producing no oscilation and in making the frequency measurement impossible.

EXAMPLE 9

Procedures of Example 6 are repeated except that a polyvinyl chloride polymer film is used as an adsorption film with the result that frequency change due to adsorption is 490 Hz corresponding to 515 ng of odor substances and bitter substances adsorbed.

COMPARATIVE EXAMPLE 12

The same frequency measurement procedures as in Example 9 are repeated except that the crystal oscillator is not covered with the barrier, resulting in producing no oscillation and in making the frequency measurement impossible.

EXAMPLE 10

Procedures of Example 7 are repeated except that a polyvinyl chloride polymer film is used as an adsorption film with the result that frequency change due to adsorption is 820 corresponding to 872 ng of odor substances and bitter substances absorbed.

COMPARATIVE EXAMPLE 13

The same frequency measurement procedures as in Example 10 are repeated except that the crystal oscillator is not covered with the barrier, resulting in producing no oscillation and in making the frequency measurement impossible.

EXAMPLE 11

Procedures of Example 1 are repeated except that polystyrene is used in place of the polyion complex to obtain a one side barrier-covered crystal oscillator.

EXAMPLE 12

The one side barrier-covered crystal oscillator obtained in Example 11 is dipped into a physiological saline solution to measure its frequency. Thereafter, ethylalcohol is added to the physiological saline solution to such an amount to be 20% by weight to adsorb the ethylalcohol onto the polymer film, followed by measuring its frequency as it is, resulting in that frequency change due to adsorption is 600 Hz corresponding to 630 ng of ethylalcohol adsorbed.

COMPARATIVE EXAMPLE 14

The same frequency measurement procedures as in Example 12 are repeated except that the crystal oscillator is not covered with the barrier, resulting in producing no oscillation in making the frequency measurement impossible.

EXAMPLE 13

Procedures of Example 12 are repeated except that a polyvinyl chloride polymer film is used as an adsorption film with the result that frequency change due to adsorption is 510 Hz corresponding to 536 ng of odor substances and bitter substances adsorbed.

COMPARATIVE EXAMPLE 15

The same frequency measurement procedures as in Example 13 are repeated except that the crystal oscillator is not covered with the barrier, resulting in producing no oscillation and in making the frequency measurement impossible.

What is claimed is:

1. A method of determining the amount of the substance or ions contained in one of an ionic solution and a non-deionized solution by use of a one side barrier-covered crystal oscillator, said method comprising the steps of:
  covering over one of two electrodes of the crystal oscillator through a predetermined insulative space substantially without being brought into contact therewith with a barrier to prevent the one of the ionic solution and the non-deionized solution from permeating therethrough,
  casting an absorption film onto the other electrode of the crystal oscillator,
  dipping the one side barrier-covered crystal oscillator into the one of the ionic solution and the non-deionized solution,
  one of absorbing the substances contained in the one of the ionic solution and the non-deionized solution onto the absorption film and chemically bonding the ions therein with the absorption film, and
  measuring frequency changes before and after the one of absorption and chemical bonding in situ in a state that the barrier-covered crystal oscillator is dipped in the one of the ionic solution and the non-deionized solution to determine the amount of the substances or ions contained in the one of the ionic solution and the non-deionized solution.

2. A method as claimed in claim 1, wherein said ionic solution is selected from the group consisting of physiological saline solution, blood, serum and body fluids.

3. A method as claimed in claim 1, wherein the substances contained in the ionic solution or the non-deionized solution are odor substances and/or bitter substances.

4. A method as claimed in claim 1, wherein the predetermined insulative space is in the range of from 0.5 mm to 5 mm as a distance from the surface of the electrode in the direction normal to the adjacent surface of the barrier.

5. A method as claimed in claim 1, wherein the ions contained in the ionic solution are bivalent metal ions and the absorption film is an immobilized bilayer film being a phosphoethanolamine based phospholipid bilayer film.

6. A method as claimed in claim 1, wherein the barrier is formed by one of adhering one of a single side of a silicone rubber and a single side of a plastic material onto the plate of the crystal oscillator around the one electrode with a silicone based polymer adhesive followed by adhering on another side of the one of silicone rubber and plastic material a plastic sheet with the silicone based polymer adhesive, and, adhering a plastic sheet on one of a silicone rubber and plastic material with the silicone based polymer adhesive followed by adhering one of the silicone rubber and the plastic material on the crystal plate around the electrode with the silicone based adhesive so that the electrode may be covered through the predetermined insulative space with the barrier thus formed.

7. A method as claimed in claim 1, wherein the barrier is formed by adhering a plastic sheet cover onto the plate of the crystal oscillator around the one electrode with a silicone based polymer adhesive so as to be sealed and thereby form the predetermined insulative space.

8. A method as claimed in claim 1, wherein the barrier is formed integrally with the plate of the crystal oscillator so as to form the predetermined insulative space.

9. A one side barrier-covered crystal oscillator used in a method of determining the amount of the substances or ions contained in one of an ionic solution and a non-deionized solution, said one side barrier-covered crystal oscillator comprising:
  a crystal oscillator,
  a barrier to cover over one electrode of the crystal oscillator through a predetermined insulative space so as to prevent one of the ionic solution and the non-deionized solution from permeating therethrough, and
  an adsorption film cast on another electrode of the crystal oscillator
  wherein said one side barrier-covered crystal oscillator is dipped into the one of the ionic solution and non-deionized solution,
  wherein substances contained in the one of the ionic solution and the non-deionized solution are one of adsorbed onto the adsorption film and chemically bonded with the adsorption film, and
  wherein frequency changes before and after the one of adsorbing and chemical bonding are measured in situ in the state that the one side barrier-covered crystal oscillator is dipped in the solution to determine an amount of substances contained in the solution.

10. A barrier-covered crystal oscillator as claimed in claim 9, wherein both electrodes are gold electrodes.

11. A barrier-covered crystal oscillator as claimed in claim 9, wherein the predetermined insulative space is in the range of from 0.5 mm to 5 mm as a distance from the surface.

12. A barrier-covered crystal oscillator as claimed in claim 9, wherein the barrier comprises one of a silicone rubber and a plastic material, one side of which is adhered onto the plate of the crystal oscilator around the one electrode and a plastic sheet adhered to a second side of the one of the silicone rubber and plastic material so as to be sealed and thereby form the predetermined insulative space.

13. A barrier-covered crystal oscillator as claimed in claim 9, wherein the barrier is formed by adhering a plastic sheet cover onto the plate of the crystal oscillator around the on electrode with a silicone based polymer adhesive so as to be sealed and form the predetermined insulative space.

14. A barrier-covered crystal oscillator as claimed in claim 9, wherein the barrier is formed integrally with the plate of the crystal oscillator by allowing a crystal plate cover to be joined with the crystal plate so as to form the predetermined insulative space.

* * * * *